United States Patent
Könning et al.

(10) Patent No.: US 9,915,595 B2
(45) Date of Patent: Mar. 13, 2018

(54) GAS-SAMPLING PROBE AND METHOD FOR OPERATING A GAS-SAMPLING PROBE

(71) Applicant: THYSSENKRUPP INDUSTRIAL SOLUTIONS AG, Essen (DE)

(72) Inventors: Ludwig Könning, Ahlen-Vorhelm (DE); Michael Streffing, Lippetal-Hovestadt (DE); Heinz Bredemeier, Sassenberg (DE); Alfons Leuer, Oelde (DE)

(73) Assignee: THYSSENKRUPP INDUSTRIAL SOLUTIONS AG, Essen (DE)

( * ) Notice: Subject to any disclaimer, the term of this patent is extended or adjusted under 35 U.S.C. 154(b) by 0 days.

(21) Appl. No.: 14/913,353

(22) PCT Filed: Jul. 31, 2014

(86) PCT No.: PCT/EP2014/002100
§ 371 (c)(1),
(2) Date: Feb. 19, 2016

(87) PCT Pub. No.: WO2015/024625
PCT Pub. Date: Feb. 26, 2015

(65) Prior Publication Data
US 2016/0209306 A1    Jul. 21, 2016

(30) Foreign Application Priority Data
Aug. 19, 2013 (DE) .................. 10 2013 108 926

(51) Int. Cl.
*G01N 1/42*    (2006.01)
*G01N 1/22*    (2006.01)
*G01N 33/00*   (2006.01)

(52) U.S. Cl.
CPC ............... *G01N 1/42* (2013.01); *G01N 1/22* (2013.01); *G01N 33/0016* (2013.01); *G01N 2001/2282* (2013.01)

(58) Field of Classification Search
CPC .................................. G01N 1/42; G01N 1/22
(Continued)

(56) References Cited

U.S. PATENT DOCUMENTS 3,460,393 A    8/1969    Putnam

FOREIGN PATENT DOCUMENTS

| AT | 9667 U1 | 1/2008 | |
| DE | 3545491 A1 * | 7/1987 | ........... G01N 1/2258 |

(Continued)

OTHER PUBLICATIONS

German language International Search Report for International patent application No. PCT/EP2014/002100; dated Oct. 20, 2014.

(Continued)

*Primary Examiner* — Harshad R Patel
*Assistant Examiner* — Jamel Williams
(74) *Attorney, Agent, or Firm* — thyssenkrupp North America, Inc.

(57) ABSTRACT

A method for operating a gas sampling probe includes removing a gas to be analyzed from a process space in the region of a front end of a gas sampling tube and conducting it through the gas sampling tube as far as a rear end and, in the process, cooling it by passing cooling air between the gas sampling tube and at least one outer casing enclosing the gas sampling tube. The cooling air is fed and discharged at the rear end of the gas sampling tube and the temperature of the gas to be analyzed is higher in the region of the front end of the gas sampling tube than the temperature of the fed cooling air, and the gas sampling probe emits outward, wherein the (Continued)

temperature of the fed cooling air is higher than the temperature of the discharged cooling air.

20 Claims, 10 Drawing Sheets

(58) Field of Classification Search
USPC .......................................... 73/863.11, 86.71
See application file for complete search history.

(56) References Cited

FOREIGN PATENT DOCUMENTS

| DE | 29608694 U1 | 9/1996 |
|---|---|---|
| DE | 10315996 A1 | 10/2004 |
| DE | 10354188 A1 | 6/2005 |
| FR | 2715732 A1 | 8/1995 |

OTHER PUBLICATIONS

English translation of International Search Report for International patent application No. PCT/EP2014/002100; dated Oct. 20, 2014.
German language Written Opinion of the International Search Authority for International patent application No. PCT/EP2014/002100; dated Oct. 20, 2014.
English translation of the Written Opinion of the International Search Authority for International patent application No. PCT/EP2014/002100; dated Oct. 20, 2014.
English translation of abstract of DE 3545491 A1.
English machine translation of specification of AT 9667 U1.
English machine translation of specification of DE 29608694 U1.
English translation of abstract of FR 2715732 A1.
English machine translation of specification of DE 10315996 A1.
English translation of abstract of DE 10354188 A1.

* cited by examiner

GAS-SAMPLING PROBE AND METHOD FOR OPERATING A GAS-SAMPLING PROBE

CROSS REFERENCE TO RELATED APPLICATIONS

This application is a U.S. National Stage Entry of International Patent Application Serial Number PCT/EP2014/002100, filed Jul. 31, 2014, which claims priority to German patent application no. DE 102013108926.7 filed Aug. 19, 2013, the entire contents of both of which are incorporated herein by reference.

FIELD

The invention relates to a gas sampling probe and to a method for operating a gas sampling probe, wherein a gas to be analyzed is removed from a process space in the region of a front end of a gas sampling tube and is conducted through the gas sampling tube as far as a rear end and in the process is cooled.

BACKGROUND

A probe for removing a gas sample from a hot reaction space is known from DE 103 15 996 A1, wherein cooling water flows through an annular space bounded by an outer casing. Since the boiling point of the water must not be reached, the maximum return temperature is around 90° C. However, at these low temperatures, it is not possible to reliably rule out situations in which the temperature drops below the dew point within the gas sampling probe. Therefore, some manufacturers additionally heat the gas sampling tube electrically, in order in this way to prevent situations in which the temperature drops below the dew point in the measurement gas. In DE 103 15 996 A1, the temperature is prevented from dropping below the dew point in that the gas sampling tube is surrounded by an evacuable cavity. However, strong water cooling also has the further drawback that the outer part of the gas sampling probe is cooled to an unnecessarily great extent, wherein an excessively cold tip of the gas sampling probe can tend toward the formation of deposits in the hot process gas.

Also known are oil-cooled gas sampling probes which use a heat transfer oil for cooling. The difference from the water circuit is that the heat transfer oil can be used in higher temperature ranges. As a result, it is possible to dispense with additional heating of the gas sampling tube. A problem, however, is that it is difficult to assess the heat transfer oil with regard to leaks, since it is not possible to rule out a fire hazard here.

Furthermore, a high-temperature sampling probe is known from DE 103 54 188 A1, wherein a gas sampling tube is enclosed by an outer tube and pressurized cooling air is conducted between these two tubes. In the process, care was taken to ensure that the removed gas to be analyzed is not cooled to below 250° along the gas sampling tube and so condensation is avoided.

Accordingly there is a need for a method of operating a gas sampling probe, by which sufficient cooling of the front end of the gas sampling tube is ensured but reliably avoids dropping the temperature of the gas to be analyzed and the components thereof below their dew point temperature.

BRIEF DESCRIPTION OF THE DRAWINGS

The present disclosure is described in detail below with reference to the attached drawing figures, wherein:

FIG. 2a is a side cross section view an embodiment of a gas sampling probe of the present disclosure, taken about a longitudinal axis thereof;

FIG. 2b is an end cross section view of the gas sampling probe of FIG. 2a, taken along section line G-G in FIG. 2a;

FIG. 3a is a side cross section view an alternate embodiment of a gas sampling probe of the present disclosure, taken about a longitudinal axis thereof;

FIG. 3b is an end cross section view of the gas sampling probe of FIG. 3a, taken along section line J-J in FIG. 3a;

FIG. 5 is a schematic side cross section view of an embodiment of an installed gas sampling probe of the present disclosure, which simultaneously shows an overlaid temperature profile there through;

DETAILED DESCRIPTION

Figure 1:
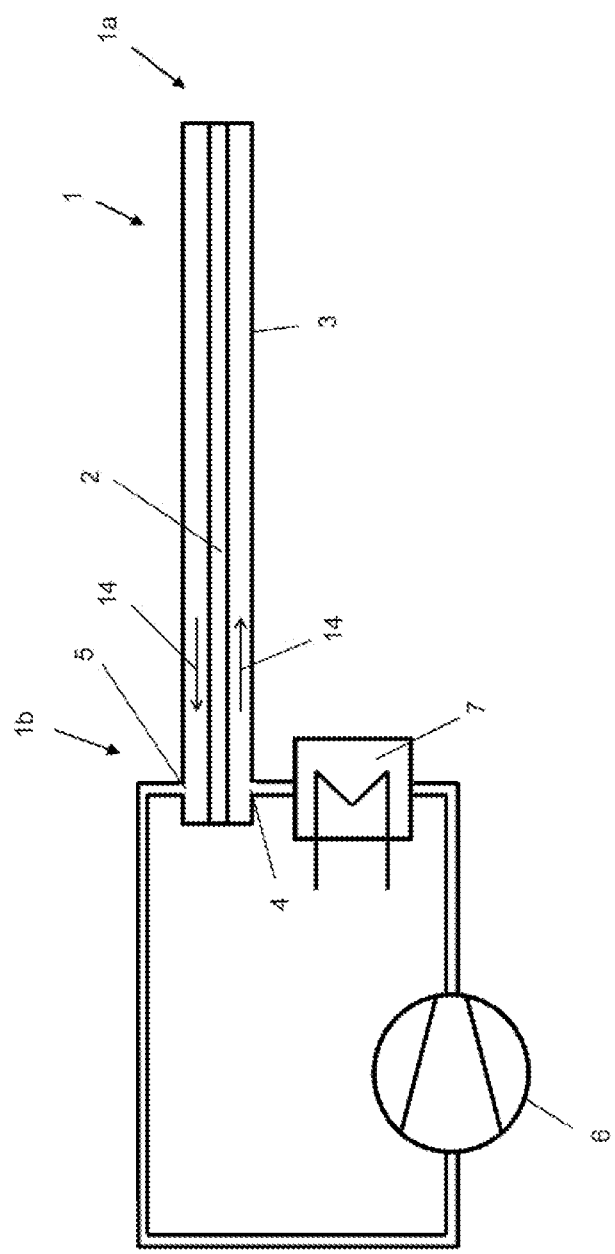
FIG. 1 is a schematic view of an embodiment of a gas sampling device of the present disclosure.

In the method according to the invention for operating a gas sampling probe, a gas to be analyzed is removed from a process space in the region of a front end of a gas sampling tube and is conducted through the gas sampling tube as far as a rear end and in the process is cooled in that cooling air is conducted between the gas sampling tube and at least one outer casing enclosing the gas sampling tube, wherein the cooling air is fed and discharged at the rear end of the gas sampling tube and the temperature of the gas to be analyzed is higher in the region of the front end of the gas sampling tube than the temperature of the fed cooling air, wherein the gas sampling probe emits outward and the temperature of the fed cooling air is higher than the temperature of the discharged cooling air.

The gas sampling device according to the invention for carrying out the above method has a gas sampling tube in order to remove a gas to be analyzed in the region of a front end and to conduct it through the gas sampling tube as far as a rear end, wherein the gas sampling tube is enclosed by at least one outer casing such that a cooling zone that extends along the length of the gas sampling tube is formed, said cooling zone having a cooling-air feed opening and a cooling-air discharge opening in the region of the rear end of the gas sampling probe, wherein the cooling-air discharge opening and the cooling-air feed opening are connected together to form a closed circuit and the gas sampling probe emits outward. Furthermore, an air heater is provided between the cooling-air discharge opening and the cooling-air feed opening.

The concept according to the invention in which the temperature of the fed cooling air is higher than the temperature of the discharged cooling air is based on the exploitation of the fact that only small quantities of heat are removed from the process and on the heat losses of the gas sampling probe towards the outside. The cooling air conducted through the gas sampling tube has the effect that the temperature of the front end of the gas sampling probe is reduced, while the gas sampling tube is heated in the rear region. At the same time, the removed gas to be analyzed is cooled from the front to the rear end. Thus, the temperature of the gas sampling tube is equalized along its entire length.

By way of air cooling, compared with water cooling, the temperature of the front end of the gas sampling tube can be raised in a targeted manner in order to reduce the risk of external material deposits. This is because, in the case of water cooling, the surface temperature of the gas sampling probe is much lower, since the heat transfer coefficient between water and the probe wall is much greater than between air and the probe wall. In addition, water can dissipate more heat on account of the greater heat capacity. Moreover, in the case of the solution according to the invention, material deposits or condensation in the gas sampling tube are likewise minimized by the higher operating temperatures.

Further configurations of the invention are the subject matter of the dependent claims.

The gas sampling probe is preferably arranged at the process space such that it absorbs heat from the outside in a front region facing the process space and emits heat to the outside in a rear region, wherein, in an overall heat balance, the gas sampling probe emits more heat than it absorbs.

The difference between the heat absorbed and emitted by the gas sampling probe corresponds to the sum of the cooling heat of the gas to be analyzed and of the cooling air.

According to a preferred configuration of the invention, the cooling air is conducted from the rear to the front end of the gas sampling tube and back again. Furthermore, the cooling air can be conducted in a circuit, wherein the temperature of the discharged cooling air is increased before it is fed again. In this case, provision can also be made for the temperature of the discharged cooling air to be measured and an air heater to be actuated depending on the temperature measured such that the temperature of the cooling air conducted in a circuit is at a prescribed setpoint value in the region of the feed at the rear end of the gas sampling tube. The temperature of the cooling gas to be fed and the quantity thereof are set such that the gas to be analyzed is cooled from the front to the rear end of the gas sampling tube at most to a minimum temperature that is greater than or equal to the dew point temperature of the components contained in the gas to be analyzed. Furthermore, provision can be made for the temperature of the fed cooling air to be higher at the rear end of the gas sampling tube than the temperature of the gas to be analyzed and the temperature of the discharged cooling air to be less than or equal to the temperature of the gas to be analyzed. By way of the temperature and quantity of the cooling air, the temperature profile of the gas sampling tube along its entire length is set such that the minimum temperature is greater than or equal to the dew point temperature of the components contained in the gas to be analyzed. Depending on the temperature of the gas to be analyzed, the temperature of the discharged cooling air is increased by at least 20° C., preferably by at least 50° C., most preferably by at least 75° C., before it is fed again. The temperature of the fed cooling air is preferably set in a range from 100° C. to 600° C. in the region of the rear end of the gas sampling tube. The temperature of the gas to be analyzed can be in a range from 200° C. to 1600° C. in the process space, i.e. prior to removal. The gas sampling probe is furthermore operated with cooling air such that the temperature of the gas removed and to be analyzed is cooled by at least 50%, preferably by at least 60%, most preferably by at least 70%, from the front to the rear end of the gas sampling tube. Furthermore, it is expedient to keep the temperature of the discharged cooling air less than or equal to the temperature of the gas sampling tube in the region of the rear end of the gas sampling tube.

The air heater is expediently connected to a control device which actuates the air heater in dependence on a temperature signal from a temperature measuring device, wherein the temperature measuring device senses the temperature of cooling air discharged via the cooling-air discharge opening. According to a first exemplary embodiment of the gas sampling probe, the cooling zone formed between the gas sampling tube and the outer casing is divided into two halves that extend along the length of the gas sampling tube, said halves being connected together in the front region of the gas sampling tube via an overflow region and the cooling-air feed opening and the cooling-air discharge opening each being provided on one of the two halves in the rear region of the gas sampling probe. According to a second exemplary embodiment, the cooling zone formed between the gas sampling tube and the outer casing has two annular spaces that are arranged concentrically with one another, said annular spaces being connected together in the front region of the gas sampling tube via an overflow region, and the cooling-air feed opening and the cooling-air discharge opening are each attached to one of the two annular spaces in the rear region of the gas sampling probe.

The maximum temperature of the gas to be analyzed is given by the temperature in the process space from which the gas is drawn. For the application case of a gas analysis in the inflow region of a furnace for producing cement clinker, this temperature is around 1200° C. When the gas to be analyzed is removed through the gas sampling tube, it must be ensured that the gas does not condense. The minimum temperature of the gas to be analyzed is therefore defined by the lowest dew point of the gaseous components within the gas. For the abovementioned application case for the gas analysis in the inflow region of a furnace for producing cement clinker, a gas temperature of about 200° C. is above the dew points to be expected. Moreover, the temperature of the gas sampling tube should be as high as possible in order to minimize the formation of deposits. The maximum wall temperature in the region of the front end of the gas sampling tube is determined by the desired creep strength of the material used. An air-cooled gas sampling probe can be operated with much higher wall temperatures than liquid-cooled gas sampling tubes, and so temperatures in the front region of 500° C. to 600° C. can be set.

The minimum wall temperature along the gas sampling tube should not drop below the lowest dew point temperature of the components in the gas to be analyzed. The setting of the minimum temperature of the removed gas to be analyzed and the distribution of the heat along the gas sampling tube are determined substantially by the temperature of the fed cooling gas and the cooling-air quantity or flow rate and have to be adapted to the respective conditions. In order to ensure an optimum distribution of the heat along the gas sampling tube, the cooling air should be conducted within the gas sampling probe at a flow rate that is so high as to result in turbulent flow.

The gas sampling device illustrated in FIG. 1 has a gas sampling probe 1 with a gas sampling tube 2 in order to remove a gas to be analyzed from a process space in the region of a front end 1a and to conduct it through the gas sampling tube as far as a rear end 1b. The gas sampling tube is enclosed by an outer casing 3, wherein cooling air 14 is conducted between the gas sampling tube 2 and outer casing 3, said cooling air 14 being fed via a cooling-air feed opening 4 at the rear end 1b and discharged via a cooling-air discharge opening 5. The cooling-air discharge opening and the cooling-air feed opening are connected together in order to form a closed circuit, wherein a fan 6 and an air heater 7 are provided in between.

Figure 2:
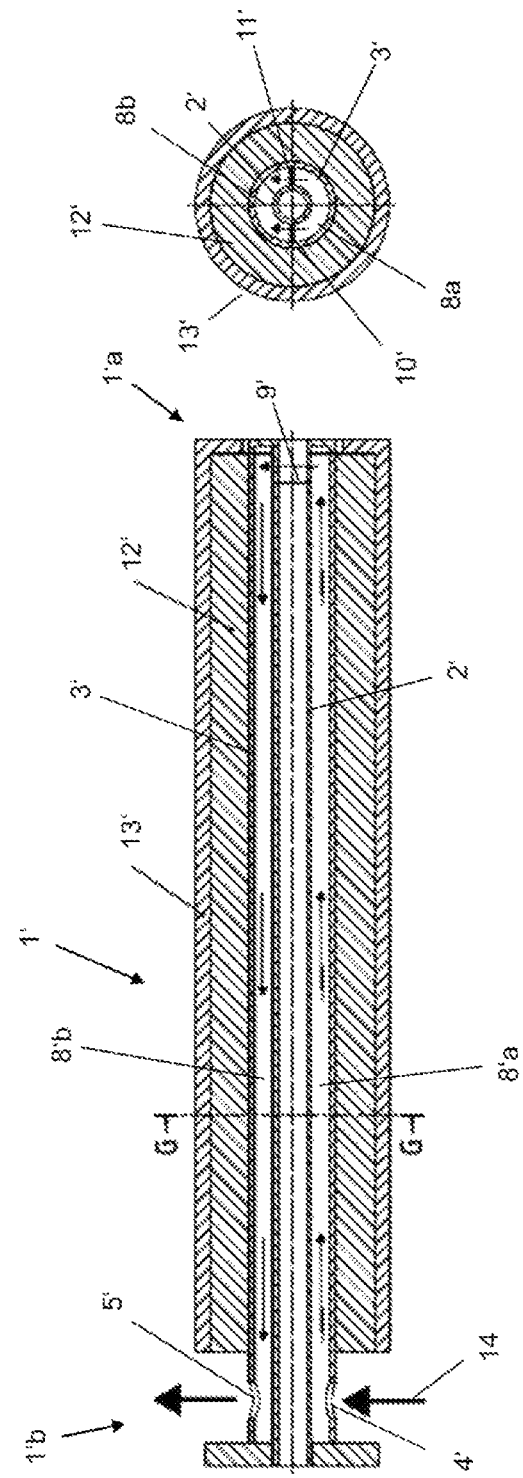

A gas sampling probe 1' according to a first exemplary embodiment is illustrated in more detail in FIGS. 2a and 2b, in which the cooling zone formed between the gas sampling tube 2' and outer casing 3' is divided into two halves 8'a, 8'b that extend along the length of the gas sampling tube 2', said halves being connected together in the front region 1'a of the gas sampling probe via an overflow region 9'. The cooling-air feed opening 4' is attached to one half 8'a and the cooling-air discharge opening 5' is attached to the other half 8'b in the rear region of the gas sampling probe. The cooling air 14 fed via the cooling-air feed opening 4' thus flows from the rear end 1'b of the gas sampling probe 1', in the lower half 8'a of the cooling zone, as far as the front region 1'a and passes there, via the overflow region 9', into the upper half 8'b of the cooling zone, and flows back there to the cooling-air discharge opening 5'. The two halves are delimited in this case by partition walls 10', 11' (FIG. 2b).

In order to protect the gas sampling probe 1' from excessive heat input from the outside, i.e. as a result of the installation situation, the outer casing 3' is enclosed by an insulation 12' and a protective tube 13'. The flow of the cooling air 14 fed by the cooling-air feed opening 4' is illustrated by way of arrows within the cooling zone.

Figure 3:
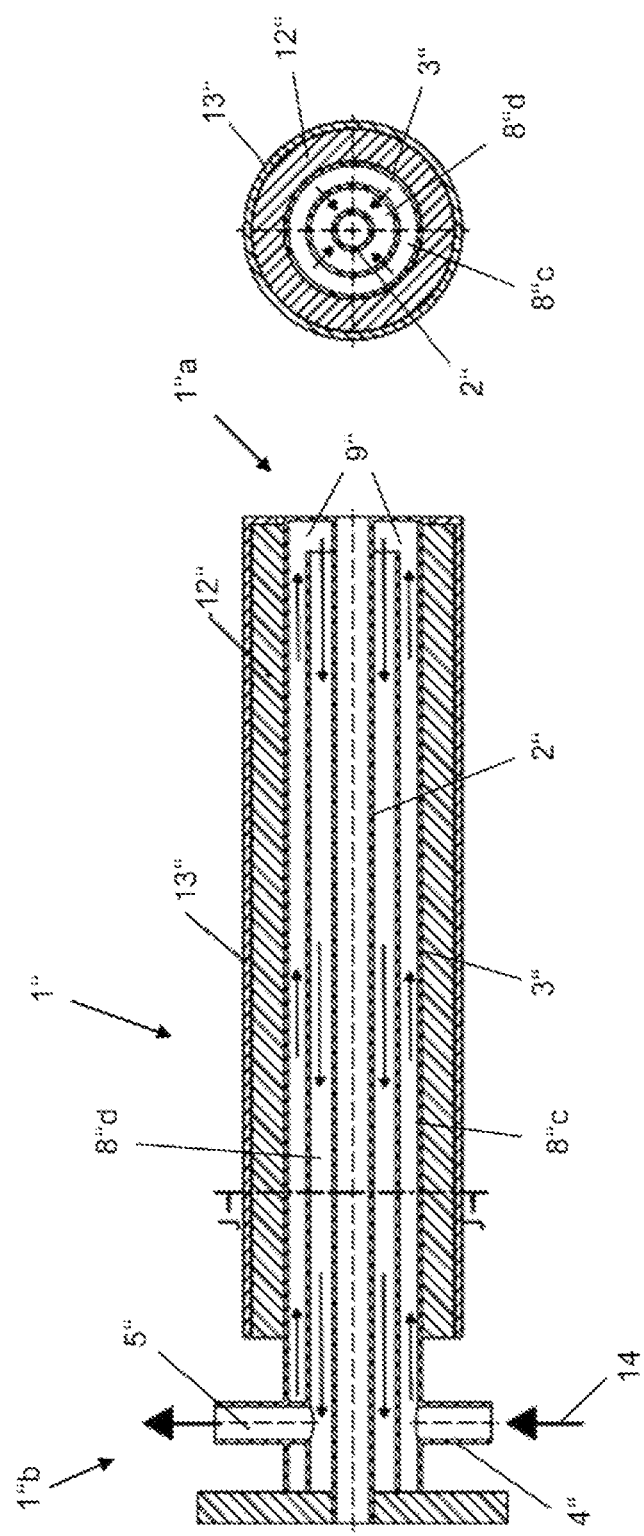

A gas sampling probe 1" according to a second exemplary embodiment is disclosed in FIGS. 3a and 3b, said gas sampling probe 1" differing substantially only by the formation of the cooling zone. The cooling zone formed between the gas sampling tube 2" and the outer casing 3" is formed in this case by two concentrically arranged annular spaces 8"c and 8"d which are again connected together in the front region 1"a of the gas sampling probe 1" via an overflow region 9". The cooling-air feed opening 4" and the cooling-air discharge opening 5" are each attached to one of the two annular spaces 8"c, 8"d in the rear region 1"b of the gas sampling probe 1". The flow of the cooling air 14 fed via the cooling-air feed opening 4" is illustrated by way of arrows within the cooling zone.

Figure 4:
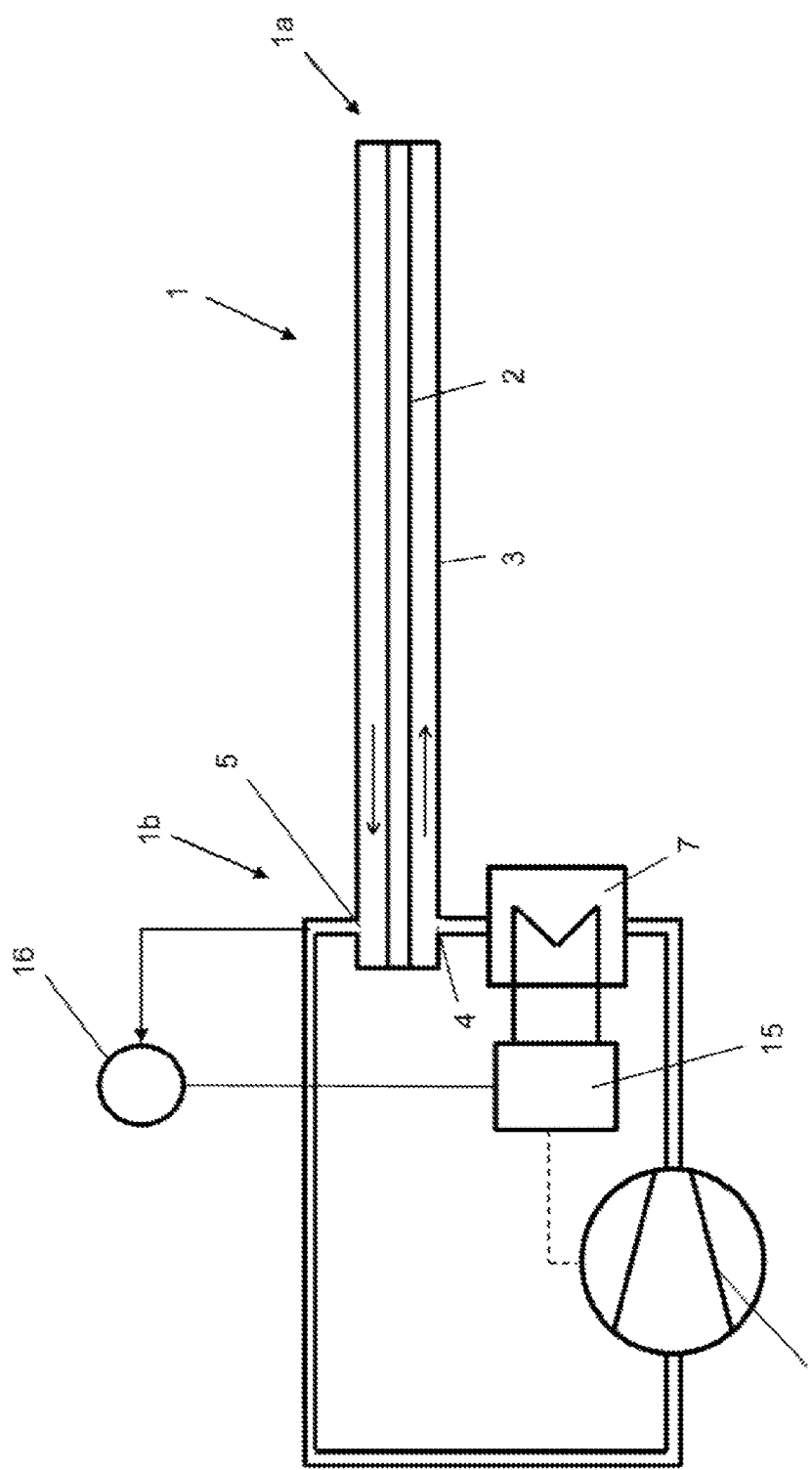
FIG. 4 is a schematic view of an embodiment of a gas sampling device having a control device configured to actuate an air heater based on a received temperature signal.

FIG. 4 shows the gas sampling device according to FIG. 1, but additionally having a control device 15 which is connected to the air heater 7 and actuates the air heater in dependence on a temperature signal from a temperature measuring device 16, wherein the temperature measuring device 16 senses the temperature of cooling air discharged via the cooling-air feed opening 5. The control device 15 can furthermore actuate the fan 6 in order as a result to regulate the cooling-air quantity/flow rate of the cooling air.

Figure 5:
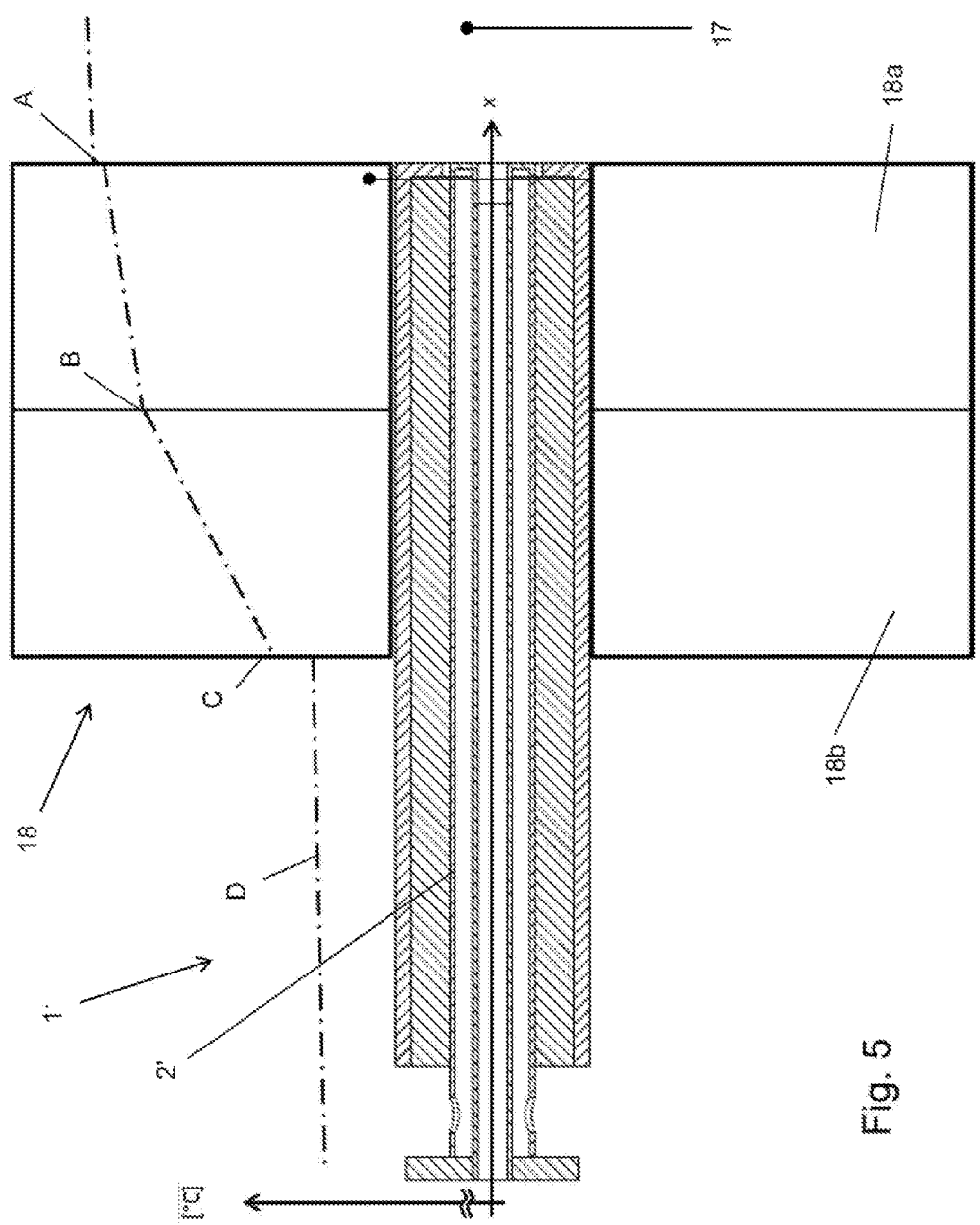

FIG. 5 shows the gas sampling probe 1' from FIG. 2a in a specific installation situation in a wall 18 enclosing a process space 17. In the exemplary embodiment illustrated, the gas sampling probe 1' leads into the process space 17 in a manner flush with the wall 18. Furthermore, the temperature profile outside the gas sampling probe is illustrated. The wall is constructed in a two-layered manner in the exemplary embodiment illustrated, wherein an inwardly directed refractory lining 18a and an insulation 18b and optionally a further housing wall are provided. Proceeding from a situation in which the gas in the process space 17 is at a temperature of about 1200° C., the temperature of the wall 18 at location A is about 1100° C. and at point B is about 960° C., while it only measures about 200° C. on the outside in the region of point C. Outside the wall, in region D, ambient temperature of for example 30° C. prevails.

Figure 6:
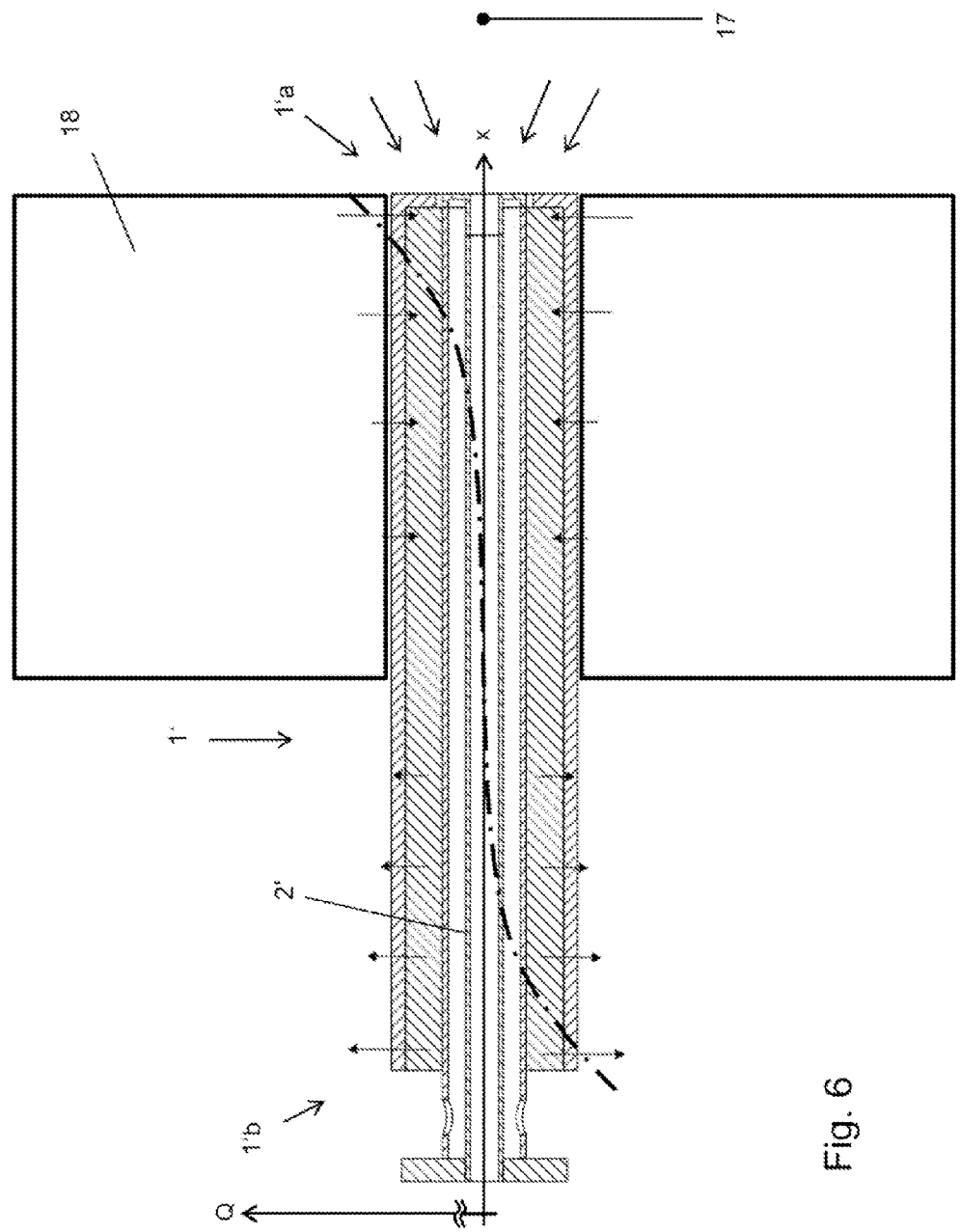
FIG. 6 is a schematic side cross section view of an embodiment of an installed gas sampling probe of the present disclosure, which simultaneously shows the heat input into the gas sampling probe.

FIG. 6 shows a diagram illustrating the heat input into the gas sampling probe as a result of the installation situation according to FIG. 5. In this case, heat is introduced in particular into the front part, plugged into the wall 18, of the gas sampling probe on account of the hot environment (wall, process space) (heat absorption region), while the rear part of the gas sampling probe emits thermal energy to the outside as a result of the contact with the ambient air (heat emission region). The heat input or heat emission is symbolized by arrows in these regions.

Figure 7:
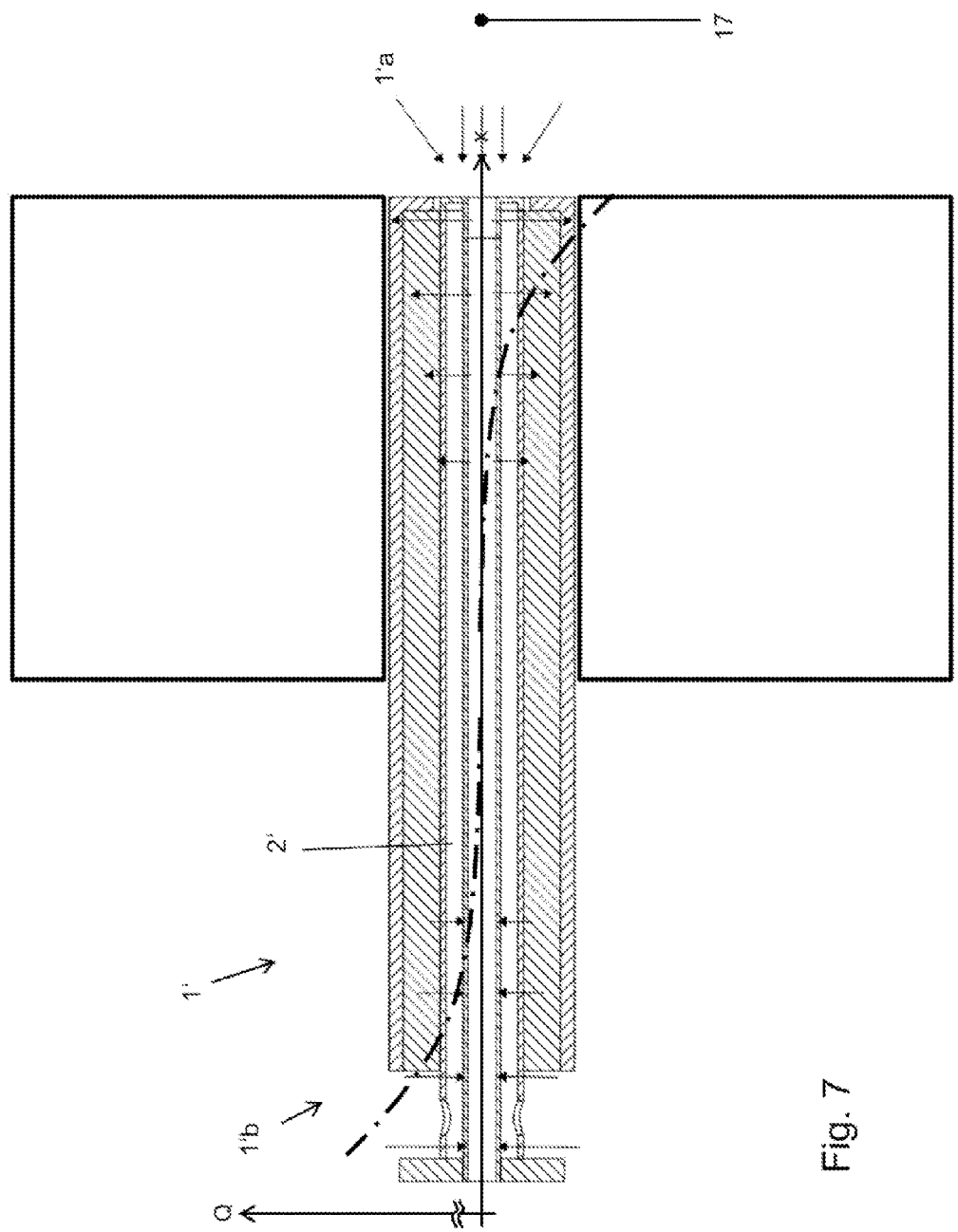
FIG. 7 is a schematic side cross section view of an embodiment of an installed gas sampling probe of the present disclosure, which simultaneously shows the heat input to the gas sampling tube.

FIG. 7 illustrates the heat input and heat output with respect to the gas sampling tube 2', wherein the hot gas sampling tube emits thermal energy to the surrounding cooling system, in particular the cooling air, in the front region having the front end 1'a, while the cooling air introduces thermal energy into the gas sampling tube in the rear region having the rear end 1'b. The thermal emission and thermal input are again symbolized by arrows in these regions.

Figure 8:
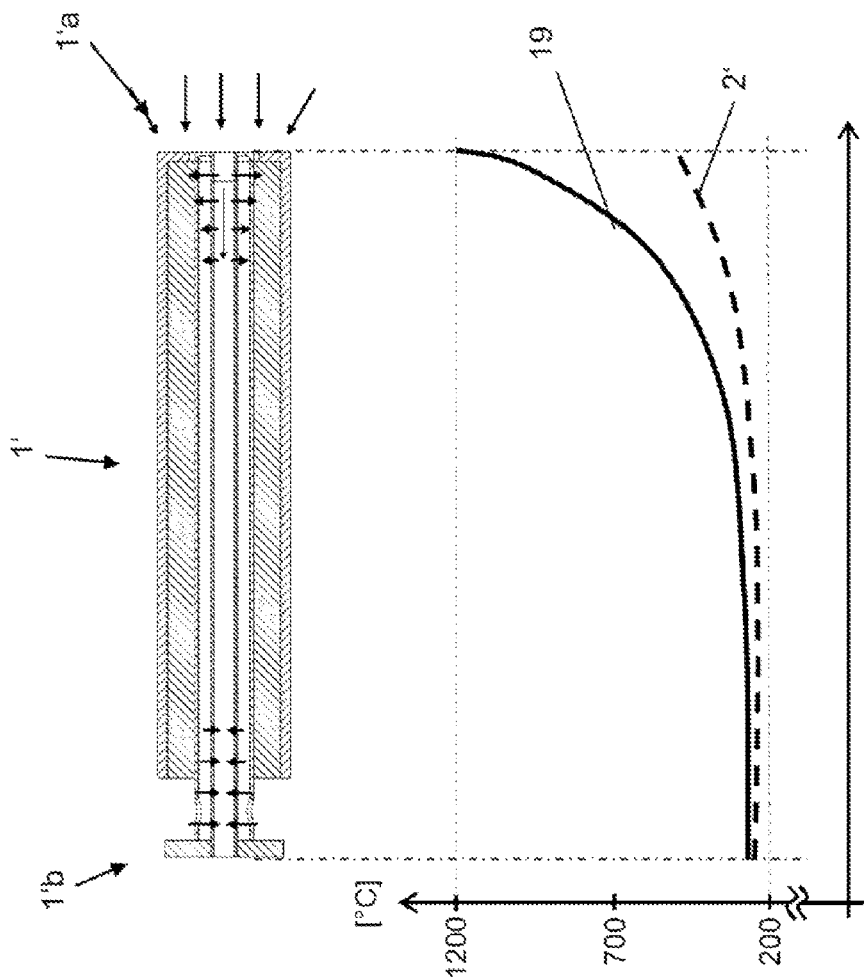
FIG. 8 is schematic side cross section view of an embodiment of a gas sampling probe of the present disclosure, and a corresponding temperature profile of the removed gas and the wall temperature of the gas sampling tube along its length.

The associated temperature profile of the removed gas 19 to be analyzed and the temperature of the gas sampling tube 2' are apparent from FIG. 8 along the length of the gas sampling probe. It can be seen that the gas 19 to be analyzed is cooled from its removal temperature at about 1200° C. to about 200° C., while the temperature of the gas sampling tube has a much lower temperature level at the front end 1'a and the temperature is adapted to the temperature of the gas 19 to be analyzed in the direction of the rear end 1'b.

Figure 9:
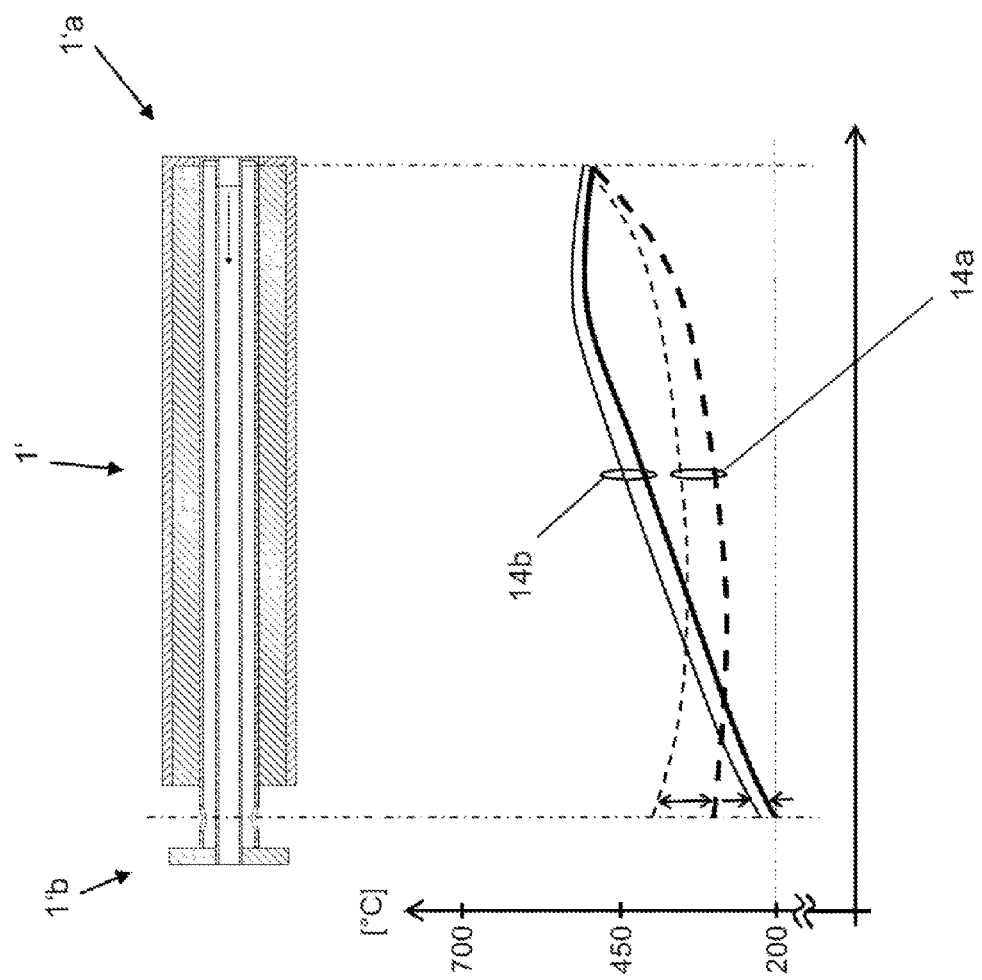
FIG. 9 is a schematic side cross section view of an embodiment of a gas sampling probe of the present disclosure, and a corresponding temperature profile of the cooling air along the length of the gas sampling tube.

Parallel thereto, FIG. 9 shows the flow temperature range 14a of the cooling air by way of dashed lines and the return temperature range 14b of the cooling air by way of solid lines. It is very clearly apparent here that the temperature of the cooling gas is higher in the region of the cooling-air feed opening than in the region of the cooling-air discharge opening. This very unusual temperature distribution is achieved in that the cooling air distributes the heat from the front region 1'a of the gas sampling probe to the rear region 1'b and simultaneously cools the 19 to be analyzed. Furthermore, the gas sampling probe emits outward, in particular in the regions in which it is not installed in the wall 18. The strong cooling action on the gas to be analyzed is based primarily also on the fact that approximately 500 times to 2500 times the quantity of cooling air is fed compared with the quantity of the gas to be analyzed. In order to be able to dissipate the heat readily from the front region 1'a to the rear region 1'b, use is expediently made of a material having high thermal conductivity, for example carbon nanotubes. The insulation 12 serves primarily to ensure that no additional heat is introduced from outside into the gas sampling probe. In order to improve the distribution of the heat along the gas sampling tube, the cooling air 14 is conducted in the gas sampling probe with turbulent flow. The required turbulent flow is generated by way of the corresponding selection of the parameters "fluid flow rate" and "viscosity", which influence the Reynolds number which is characteristic for the flow, and the surface quality of the tube wall. Furthermore, the generation of the turbulent flow could be supported by a correspondingly rough surface of the walls bounding the cooling zone.

Via the fan 6 and the air heater 7, the cooling air can be adapted to the external conditions in terms of its flow rate/quantity and its temperature, in order to avoid excessive cooling of the gas to be analyzed below the dew point temperature of the components contained in the gas to be analyzed and also to achieve equalization of the temperature profile along the gas sampling probe.

Figure 10:
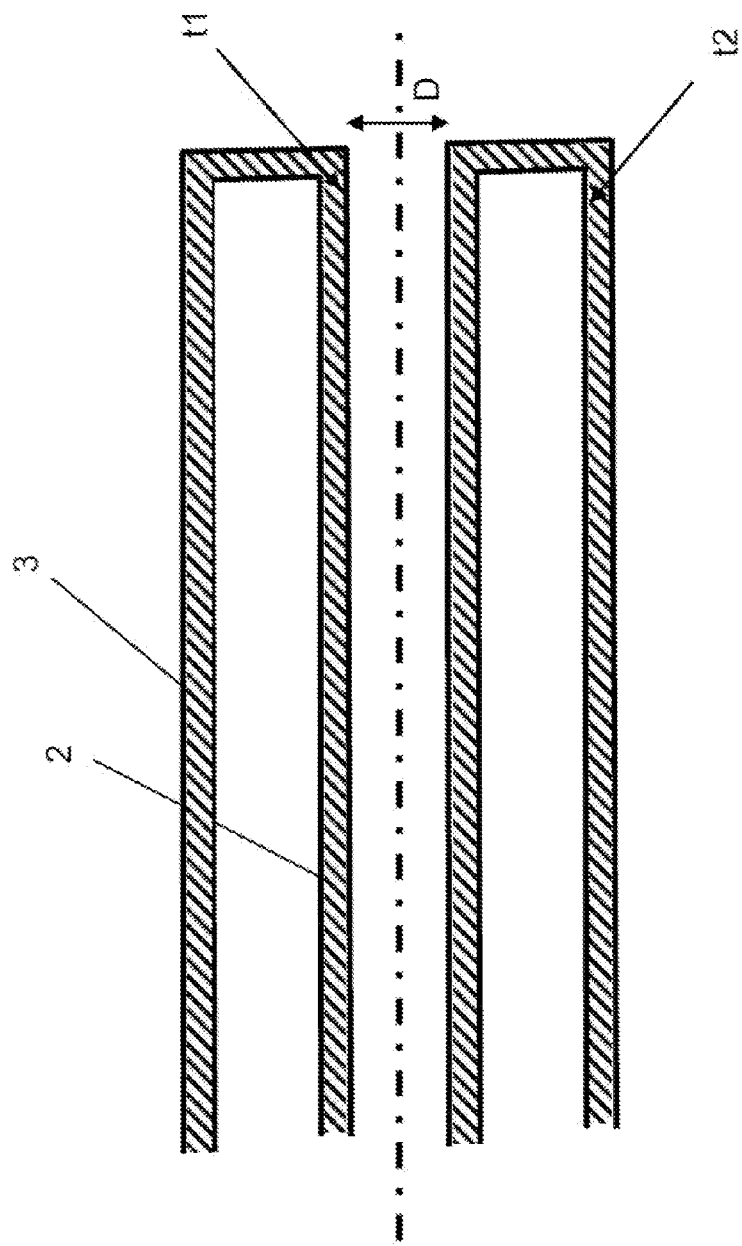
FIG. 10 is a cross section detail view of an embodiment of a front end of a gas sampling probe of the present disclosure.

With regard to FIG. 10, an explanation is given as to how both targets can be achieved. It has been found to be advantageous for the wall thickness t1 of the gas sampling tube 2 and the wall thickness t2 of the outer casing 3 to be defined with regard to the flow cross-sectional area of the gas sampling tube with the inside diameter D such that the area which is formed from the annular surfaces with the wall thicknesses t1 and t2 is greater than or equal to 0.4 times the flow cross-sectional area of the gas sampling tube.

What is claimed is:

1. A method for operating a gas sampling probe, comprising:
    removing a gas to be analyzed from a process space in a region of a front end of a gas sampling tube;
    conducting the gas to be analyzed through the gas sampling tube to a rear end thereof; and
    during said conducting step, feeding cooling air between an outer surface of the gas sampling tube and at least one outer casing enclosing the gas sampling tube, so as to simultaneously cool the gas to be analyzed that is conducted through the gas sampling tube, wherein the cooling air is fed and discharged at the rear end of the gas sampling tube and a temperature of the gas to be analyzed is higher in the region of the front end of the gas sampling tube than a temperature of the fed cooling air, and wherein the gas sampling probe at least near the rear end of the gas sampling tube emits thermal energy outward, and wherein the temperature of the fed cooling air is higher than a temperature of the discharged cooling air.

2. The method of claim 1, wherein the cooling air is conducted from the rear end to the front end of the gas sampling tube and back to the rear end.

3. The method of claim 1, wherein the cooling air is conducted in a circuit.

4. The method of claim 3, wherein the temperature of the discharged cooling air is measured and an air heater is actuated depending on the temperature measured such that the temperature of the cooling air conducted in the circuit is at a prescribed setpoint value in a region where the cooling air is fed at the rear end of the gas sampling tube.

5. The method of claim 1, wherein the temperature of the discharged cooling air is increased before the discharged cooling air is fed again.

6. The method of claim 1, wherein the gas to be analyzed is cooled from the front end to the rear end of the gas sampling tube at most to a minimum temperature that is greater than or equal to a dew point temperature of components contained in the gas to be analyzed.

7. The method of claim 1, wherein the temperature of the fed cooling air is higher at the rear end of the gas sampling tube than the temperature of the gas to be analyzed at the rear end of the gas sampling tube, wherein the temperature of the discharged cooling air is less than or equal to the temperature of the gas to be analyzed at the rear end of the gas sampling tube.

8. The method of claim 1, wherein a temperature profile of the gas sampling tube along its entire length is set such that a minimum temperature is greater than or equal to a dew point temperature of components contained in the gas to be analyzed.

9. The method of claim 1, wherein the temperature of the discharged cooling air is increased by at least 20° C. before the discharged cooling air is fed again.

10. The method of claim 1, wherein the temperature of the fed cooling air is set in a range from 100° C. to 600° C. in a region of the rear end of the gas sampling tube.

11. The method of claim 1, wherein the temperature of the gas removed and to be analyzed is cooled by at least 50% from the front end to the rear end of the gas sampling tube.

12. The method of claim 1, wherein the temperature of the discharged cooling air is less than or equal to a temperature of the gas sampling tube in a region of the rear end of the gas sampling tube.

13. The method of claim 1, wherein the gas sampling probe is arranged at the process space such that the gas sampling probe absorbs external heat in a front region and emits heat in a rear region, wherein in an overall heat balance the gas sampling probe emits more heat than the gas sampling probe absorbs.

14. The method of claim 1, wherein a difference between heat absorbed and heat emitted by the gas sampling probe corresponds to a sum of a cooling heat of the gas to be analyzed and of the cooling air.

15. A gas sampling device comprising:
    a gas sampling probe that has a gas sampling tube for removing a gas to be analyzed in a region of a front end of the gas sampling tube and to conduct the gas to be analyzed through the gas sampling tube as far as a rear end of the gas sampling tube, wherein the gas sampling tube is enclosed by at least one outer casing, which forms a cooling zone that extends along a length of the gas sampling tube, said cooling zone having in a region of the rear end of the gas sampling tube a cooling-air feed opening for feeding cooling air into the cooling zone and a cooling-air discharge opening for discharging the cooling air from the cooling zone, wherein the gas sampling probe at least near the rear end of the gas sampling tube emits thermal energy outward, wherein the cooling-air discharge opening and the cooling-air feed opening are connected to form a closed circuit and an air heater for increasing a temperature of the discharged cooling air is disposed between the cooling-air discharge opening and the cooling-air feed opening.

16. The gas sampling device of claim 15, wherein the gas to be analyzed is removed from a process space, wherein the gas sampling probe is arranged at the process space such that the gas sampling probe forms a heat absorption region in a front region of the gas sampling probe and a heat emission region in a rear region of the gas sampling probe.

17. The gas sampling device of claim 15, wherein the air heater is connected to a control device that actuates the air heater in dependence on a temperature signal from a temperature measuring device, wherein the temperature measuring device senses the temperature of the discharged cooling air.

18. The gas sampling device of claim 15, wherein the cooling zone formed between the gas sampling tube and the outer casing is divided into two halves that extend along the length of the gas sampling tube, said two halves being connected in a front region of the gas sampling probe via an overflow region and the cooling-air feed opening and the cooling-air discharge opening each being disposed on one of the two halves in a rear region of the gas sampling probe.

19. The gas sampling device of claim 15, wherein the cooling zone formed between the gas sampling tube and the outer casing has two annular spaces that are arranged concentrically with one another, said two annular spaces being connected in a front region of the gas sampling probe via an overflow region, and the cooling-air feed opening and the cooling-air discharge opening are each disposed on one of the two annular spaces in a rear region of the gas sampling probe.

20. A gas sampling device comprising:
- a gas sampling tube for conducting a gas to be analyzed from a region near a front end of the gas sampling tube to a rear end of the gas sampling tube;
- an outer casing that encloses the gas sampling tube such that a cooling zone exists between the outer casing and the gas sampling tube, wherein the cooling zone has in a region of the rear end of the gas sampling tube a cooling-air feed opening for feeding cooling air into the cooling zone and a cooling-air discharge opening for discharging the cooling air from the cooling zone, wherein the cooling-air discharge opening and the cooling-air feed opening are connected and form a part of a circuit through which the cooling air flows; and
- a heater for increasing a temperature of the cooling air that is discharged before the cooling air is fed into the cooling-air feed opening, the heater being disposed between the cooling-air discharge opening and the cooling-air feed opening.

* * * * *